US012623016B2

(12) United States Patent
Volle et al.

(10) Patent No.: US 12,623,016 B2
(45) Date of Patent: May 12, 2026

(54) PRESSURE MANAGEMENT METHOD FOR A DRUG DELIVERY DEVICE

(71) Applicant: Becton, Dickinson and Company, Franklin Lakes, NJ (US)

(72) Inventors: Jean-Marc Volle, Coublevie (FR); Steve Beguin, Rathdrum (IE); Simon O'Reilly, Dublin (IE); Raphael Marcelpoil, Saint Pierre de Chartreuse (FR); Cedrick Orny, Grenoble (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1158 days.

(21) Appl. No.: 17/527,619

(22) Filed: Nov. 16, 2021

(65) Prior Publication Data

US 2022/0152301 A1 May 19, 2022

Related U.S. Application Data

(60) Provisional application No. 63/114,894, filed on Nov. 17, 2020.

(51) Int. Cl.
*A61M 5/142* (2006.01)
*A61M 5/168* (2006.01)
(52) U.S. Cl.
CPC .... *A61M 5/14248* (2013.01); *A61M 5/14244* (2013.01); *A61M 5/16859* (2013.01);
(Continued)
(58) Field of Classification Search
CPC .......... A61M 5/16827; A61M 5/14244; A61M 5/16877; A61M 2005/14208;
(Continued)

(56) References Cited

U.S. PATENT DOCUMENTS

| | | | |
|---|---|---|---|
| 5,725,017 A | 3/1998 | Elsberry et al. | |
| 6,422,057 B1 * | 7/2002 | Anderson | F04B 51/00 604/153 |

(Continued)

FOREIGN PATENT DOCUMENTS

| | | |
|---|---|---|
| CN | 103656786 A | 3/2014 |
| CN | 104245019 A | 12/2014 |

(Continued)

OTHER PUBLICATIONS

"Insulin Overdose: Causes, Symptoms, and What to Do" by Ginger Vieira, diabetesstrong.com, Mar. 19, 2020 version (Year: 2020).*

(Continued)

*Primary Examiner* — Michael J Tsai
*Assistant Examiner* — Isabella S North
(74) *Attorney, Agent, or Firm* — The Webb Law Firm

(57) ABSTRACT

A method of pressure management for a drug delivery device including a pump, a fluid line, and a power source, includes: delivering fluid through the fluid line via the pump; determining a parameter indicative of pressure within the fluid line; determining whether the parameter indicative of pressure within the fluid line exceeds a pressure threshold level; pausing the delivery of fluid through the fluid line until a predetermined condition is satisfied; and resuming the delivery of the fluid through the fluid line after the predetermined condition is satisfied.

20 Claims, 10 Drawing Sheets

(52) U.S. Cl.
CPC .................. *A61M 5/16877* (2013.01); *A61M 2005/14208* (2013.01); *A61M 2205/3334* (2013.01); *A61M 2205/50* (2013.01)

(58) Field of Classification Search
CPC ...... A61M 2205/3334; A61M 2205/50; A61M 5/16859; A61M 5/14248; A61M 5/16831; A61M 5/16854; A61M 2005/16863; A61M 5/16881; A61M 2205/3344; A61M 2205/52; A61M 2005/16868; A61M 2005/16872; A61M 2005/14252; A61M 2205/3341; G16H 20/17
USPC ..... 604/151, 67, 131, 123, 207, 246; 702/50
See application file for complete search history.

(56) References Cited

U.S. PATENT DOCUMENTS

| | | | | |
|---|---|---|---|---|
| 6,595,756 | B2 | 7/2003 | Gray et al. | |
| 8,535,015 | B2 * | 9/2013 | Baur .................. | F04B 43/1253 |
| | | | | 600/156 |
| 9,504,790 | B1 * | 11/2016 | Hochman ............ | A61B 5/4896 |
| 10,449,292 | B2 * | 10/2019 | Pizzochero ....... | A61M 5/16831 |
| 2004/0176727 | A1 * | 9/2004 | Shekalim ............ | A61M 5/1454 |
| | | | | 604/181 |

| | | | | |
|---|---|---|---|---|
| 2007/0156086 | A1 | 7/2007 | Fentress et al. | |
| 2011/0208160 | A1 | 8/2011 | Wu et al. | |
| 2013/0238261 | A1 * | 9/2013 | Denis ................ | A61M 5/16854 |
| | | | | 702/50 |
| 2015/0153244 | A1 * | 6/2015 | Nienhoff .............. | G01M 3/025 |
| | | | | 73/40 |
| 2016/0331895 | A1 * | 11/2016 | Pope ................. | A61M 5/16854 |
| 2017/0203036 | A1 * | 7/2017 | Mazlish .................. | A61M 5/00 |

FOREIGN PATENT DOCUMENTS

| | | | |
|---|---|---|---|
| CN | 107921199 | A | 4/2018 |
| CN | 108697325 | A | 10/2018 |
| JP | H06205829 | A | 7/1994 |
| JP | 2008255990 | A | 10/2008 |

OTHER PUBLICATIONS

"Insulin Overdose: Causes, Symptoms, and What to Do" by Ginger Vieira, diabetesstrong.com, Mar. 19, 2020 version (Year: 2020) (Year: 2020).*
Cobo et al., "MEMS: Enabled Drug Delivery Systems", Advanced Healthcare Materials, 2015, pp. 1-14.

* cited by examiner

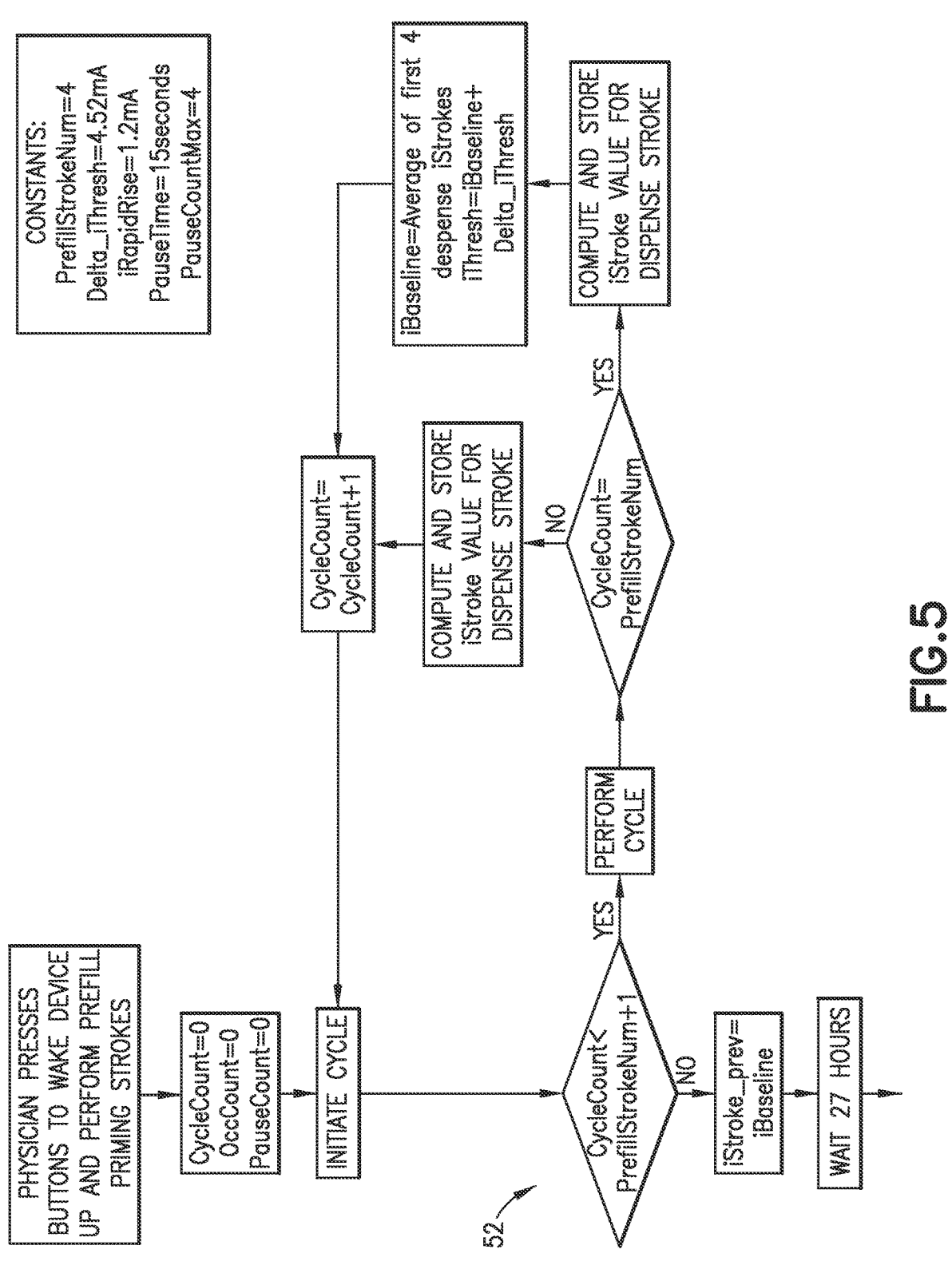

CONSTANTS:
PrefillStrokeNum=4
Delta_IThresh=4.52mA
iRapidRise=1.2mA
PauseTime=15seconds
PauseCountMax=4

PHYSICIAN PRESSES BUTTONS TO WAKE DEVICE UP AND PERFORM PREFILL PRIMING STROKES

CycleCount=0
OccCount=0
PauseCount=0

INITIATE CYCLE

52

CycleCount< PrefillStrokeNum+1

YES → PERFORM CYCLE

NO → iStroke_prev= iBaseline → WAIT 27 HOURS

CycleCount= PrefillStrokeNum

NO → COMPUTE AND STORE iStroke VALUE FOR DISPENSE STROKE

YES → COMPUTE AND STORE iStroke VALUE FOR DISPENSE STROKE iBaseline=Average of first 4 despense iStrokes
iThresh=iBaseline+ Delta_IThresh CycleCount= CycleCount+1

FIG.5

PRESSURE MANAGEMENT METHOD FOR A DRUG DELIVERY DEVICE

CROSS-REFERENCE TO RELATED APPLICATION

The present application claims priority to U.S. Provisional Application Ser. No. 63/114,894, filed Nov. 17, 2020, entitled "Pressure Management Method for a Drug Delivery Device", the entire disclosure of which is hereby incorporated by reference in its entirety.

BACKGROUND OF THE INVENTION

Field of the Invention

The present disclosure relates to a method of pressure management for a drug delivery device.

Description of Related Art

Wearable medical devices, such as automatic injectors, have the benefit of providing therapy to the patient at a location remote from a clinical facility and/or while being worn discretely under the patient's clothing. The wearable medical device can be applied to the patient's skin and configured to automatically deliver a dose of a pharmaceutical composition within a predetermined time period after applying the wearable medical device to the patient's skin, such as after a 27 hour delay. After the device delivers the pharmaceutical composition to the patient, the patient may subsequently remove and dispose of the device.

In certain circumstances, due to the medium the liquid is being injected, the flow of fluid leaving the device may be impaired, which can lead to increased pressure in the fluid line of the device. When the pressure rises above a certain threshold, the integrity of the fluid path may be compromised causing a leak within the device and a failure to deliver the full dose of medicament. A fluid leak within the device may also cause damage to the device and subsequent system failures as well as potential contamination concerns due to contact between the fluid and the device.

Human subcutaneous tissue is composed of various cell types, extracellular matrix (ECM) constituents, microstructures, and macroscopic arrangement of cells and ECM. Those elements contribute to the mechanical properties of the tissue. The tissue may also include the lymphatic system, blood vessels, and has intrinsic fluid absorption and retention properties. These characteristics vary among individuals, location within the body, and over time may cause variable degrees of resistance to the infusion of fluids at the site of injection. When the resistance of the tissue is too high or the absorption rate is too low for a given delivery flow rate from the device, the pressure may build up and reach valves above the threshold where the fluid line and other components may be compromised.

SUMMARY OF THE INVENTION

In one aspect or embodiment, a method of pressure management for a drug delivery device a pump, a fluid line, and a power source, includes: delivering fluid through the fluid line via the pump; determining a parameter indicative of pressure within the fluid line; determining whether the parameter indicative of pressure within the fluid line exceeds a pressure threshold level; pausing the delivery of fluid through the fluid line until a predetermined condition is satisfied; and resuming the delivery of the fluid through the fluid line after the predetermined condition is satisfied.

The method may be performed using a microcontroller comprising at least one processor.

The method may include terminating the delivery of fluid through the fluid line when the delivery of fluid has been paused for a maximum delay period. The maximum delay period may be at least 30 seconds. In another configuration, the maximum delay period may be at least 4 minutes. The predetermined condition may be a predetermined pressure level within the fluid line. The predetermined condition may be a predetermined period of time.

The pressure within the fluid line may be determined by measuring a parameter indicative of pressure, such as a current of the drug delivery device, during actuation of the pump. The measuring of the current of the drug delivery device may include subtracting a reference current value from a peak current value during an actuation cycle of the pump to determine a stroke current value. The predetermined condition may be an input from a sensor in the drug delivery device or an input from a user.

The method may further include initially delivering fluid through the fluid line via the pump at a first flow rate, and subsequently delivering fluid through the fluid line via the pump at a second flow rate, where the first flow rate is lower than the second flow rate. The initial delivery of fluid through the fluid line via the pump at the first flow rate may be configured to deliver 15-50 µL of fluid. The initial delivery of fluid through the fluid line via the pump at the first flow rate may include pausing the delivery of fluid for a predetermined delay period between delivery boluses. The first flow rate may correspond to a maximum acceptable flow rate assuming a fully occluded condition. The initial delivery of fluid through the fluid line via the pump at the first flow rate may be configured to deliver a maximum of 20 µL of fluid.

In a further aspect or embodiment, a drug delivery device includes a power source, a reservoir configured to receive a fluid, a fluid line in fluid communication with the reservoir, a pump configured to deliver a fluid from the reservoir to the fluid line, and a microcontroller including at least one processor programmed or configured to: deliver fluid through the fluid line via the pump; determine a parameter indicative of pressure within the fluid line; determine whether the parameter indicative of pressure within the fluid line exceeds a pressure threshold level; pause the delivery of fluid through the fluid line until a predetermined condition is satisfied; and resume the delivery of the fluid through the fluid line after the predetermined condition is satisfied.

In a further aspect or embodiment, a computer program product for a method of pressure management for a drug delivery device comprising a microcontroller, a reservoir, a pump, a fluid line, and a power source, the computer program product comprising at least one non-transitory computer-readable medium including program instructions that, when executed by the microcontroller, cause the microcontroller to: operate the drug delivery device to deliver fluid through the fluid line via the pump; determine a parameter indicative of pressure within the fluid line; determine whether the parameter indicative of pressure within the fluid line exceeds a pressure threshold level; pause the delivery of fluid through the fluid line until a predetermined condition is satisfied; and resume the delivery of the fluid through the fluid line after the predetermined condition is satisfied.

The pressure threshold level comprises a threshold, range, and/or rate of pressure increase.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 5 is a schematic view of a method of pressure management according one aspect or embodiment of the present application.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION OF THE INVENTION

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". By "about" is meant a range of plus or minus ten percent of the stated value. As used in the specification and the claims, the singular form of "a", "an", and "the" include plural referents unless the context clearly dictates otherwise. The terms "first", "second", and the like are not intended to refer to any particular order or chronology, but instead refer to different conditions, properties, or elements. By "at least" is meant "greater than or equal to".

Figure 1:
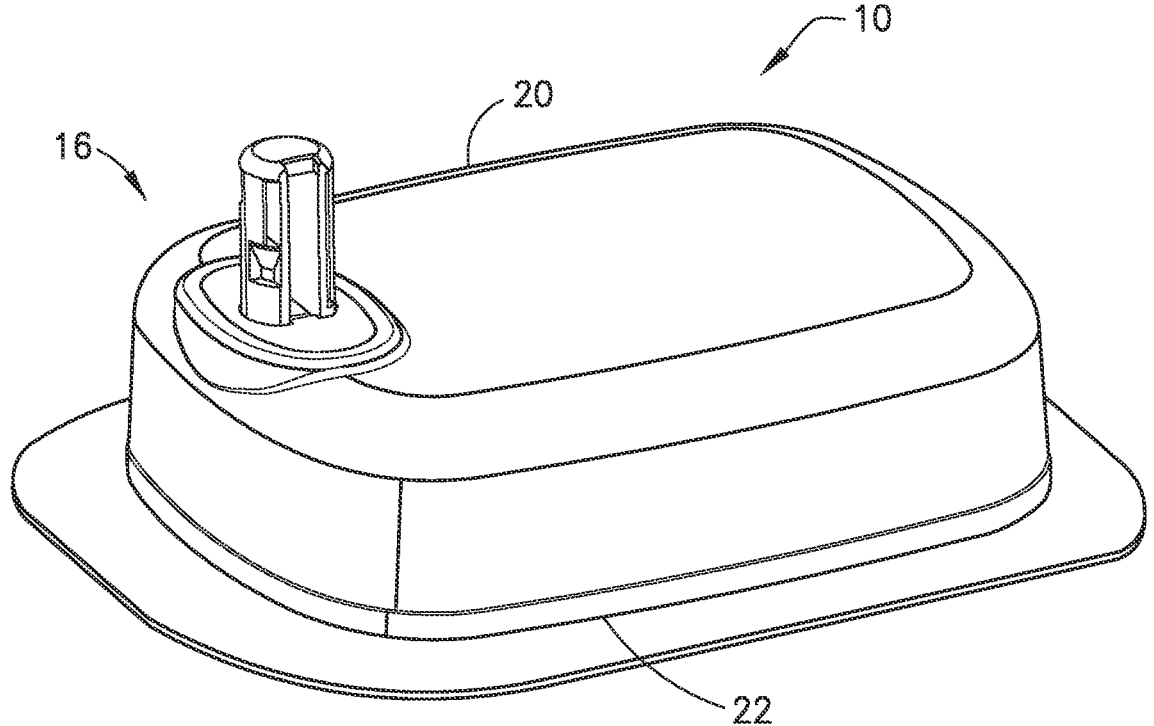
FIG. 1 is a perspective view of a drug delivery device according to one aspect or embodiment of the present application.
Figure 2:
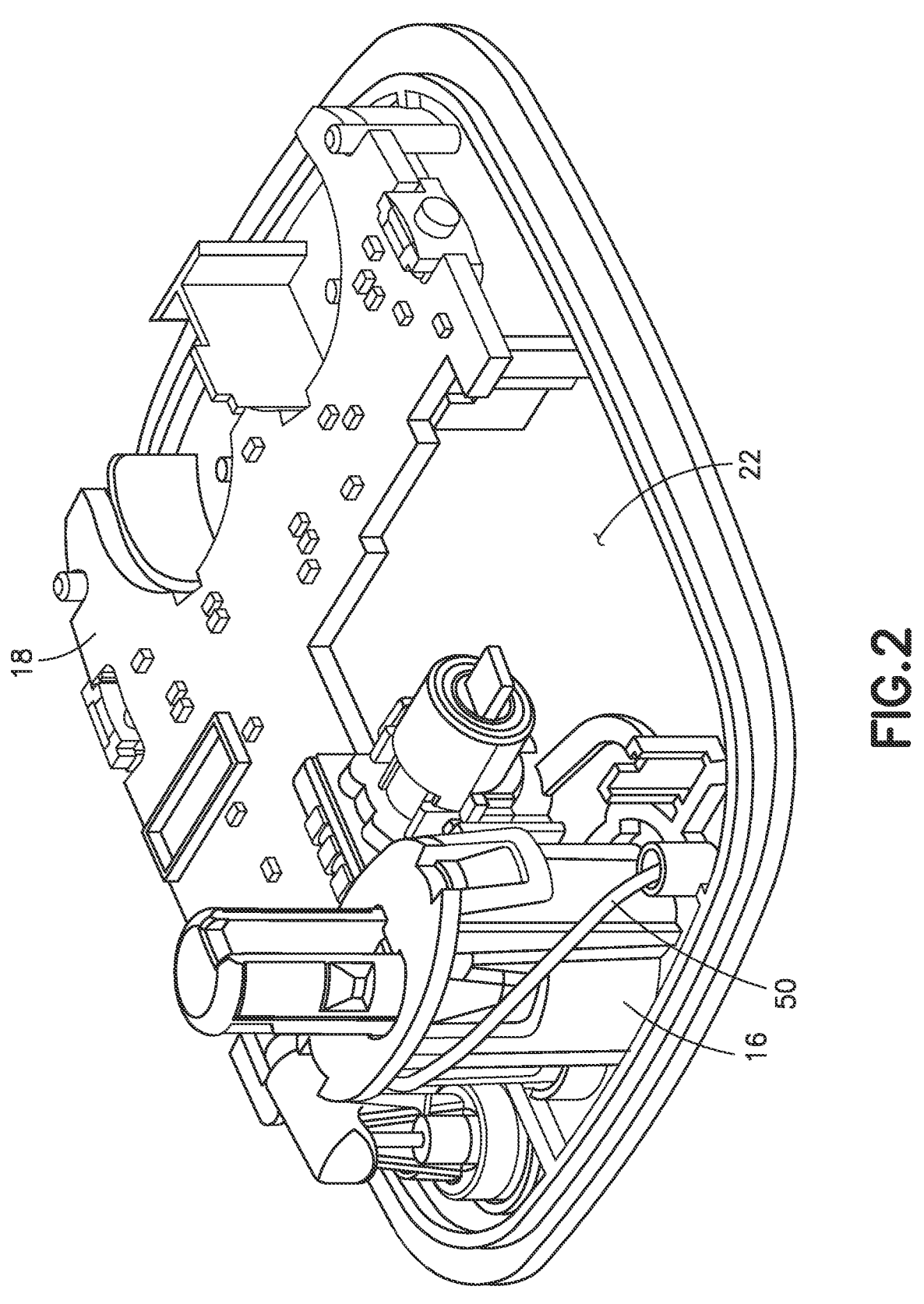
FIG. 2 is a perspective view of the drug delivery device of FIG. 1, with a top cover removed.
Figure 3:
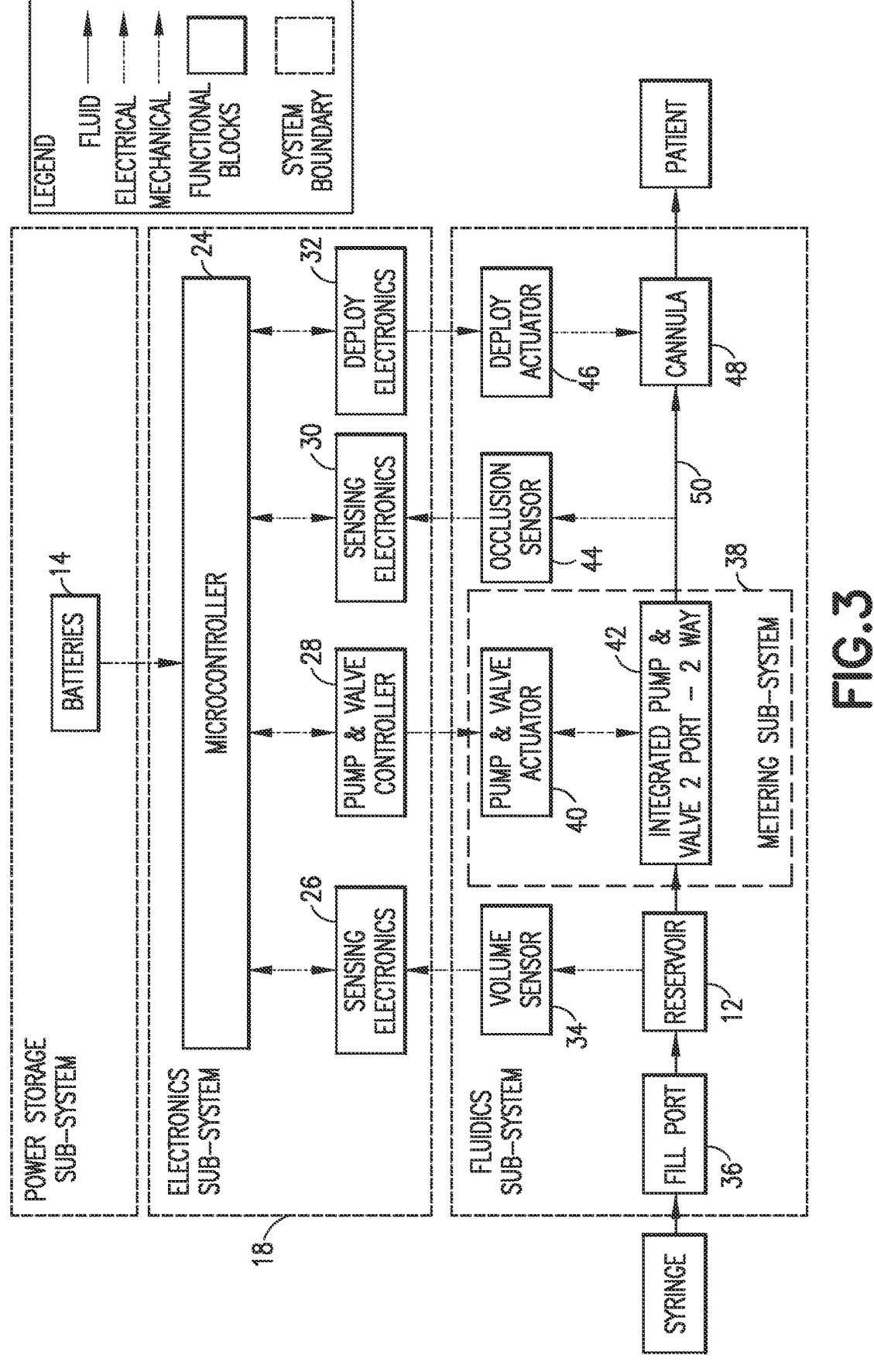
FIG. 3 is a schematic view of the drug delivery device of FIG. 1.

Referring to FIGS. 1-3, a drug delivery device 10 includes a reservoir 12, a power source 14, an insertion mechanism 16, control electronics 18, a cover 20, and a base 22. In one aspect or embodiment, the drug delivery device 10 is a wearable automatic injector, such as an insulin or bone marrow stimulant delivery device. The drug delivery device 10 may be mounted onto the skin of a patient and triggered to inject a pharmaceutical composition from the reservoir 12 into the patient. The drug delivery device 10 may be pre-filled with the pharmaceutical composition, or it may be filled with the pharmaceutical composition by the patient or medical professional prior to use.

The drug delivery device 10 is configured to deliver a dose of a pharmaceutical composition, e.g., any desired medicament, into the patient's body by a subcutaneous injection at a slow, controlled injection rate. Exemplary time durations for the delivery achieved by the drug delivery device 10 may range from about 5 minutes to about 60 minutes, but are not limited to this exemplary range. Exemplary volumes of the pharmaceutical composition delivered by the drug delivery device 10 may range from about 0.1 milliliters to about 10 milliliters, but are not limited to this exemplary range. The volume of the pharmaceutical composition delivered to the patient may be adjusted.

Referring again to FIGS. 1-4, in one aspect or embodiment, the power source 14 is a DC power source including one or more batteries. The control electronics 18 include a microcontroller 24, sensing electronics 26, a pump and valve controller 28, sensing electronics 30, and deployments electronics 32, which control the actuation of the drug delivery device 10. The drug delivery device 10 includes a fluidics sub-system that includes the reservoir 12, volume sensor 34 for the reservoir 12, a reservoir fill port 36, and a metering system 38 including a pump and valve actuator 40 and a pump and valve mechanism 42. The fluidic sub-system may further include an occlusion sensor 44, a deploy actuator 46, a cannula 48 for insertion into a patient's skin, and a fluid line 50 in fluid communication with the reservoir 12 and the cannula 48. In an alternative aspect or embodiment, the occlusion sensor is a system for measuring the motor current. In one aspect or embodiment, the insertion mechanism 16 is configured to move the cannula 48 from a retracted position positioned entirely within the device 10 to an extended position where the cannula 48 extends outside of the device 10. The drug delivery device 10 may operate in the same manner as discussed in U.S. Pat. No. 10,449,292 to Pizzochero et al.

Figure 4:
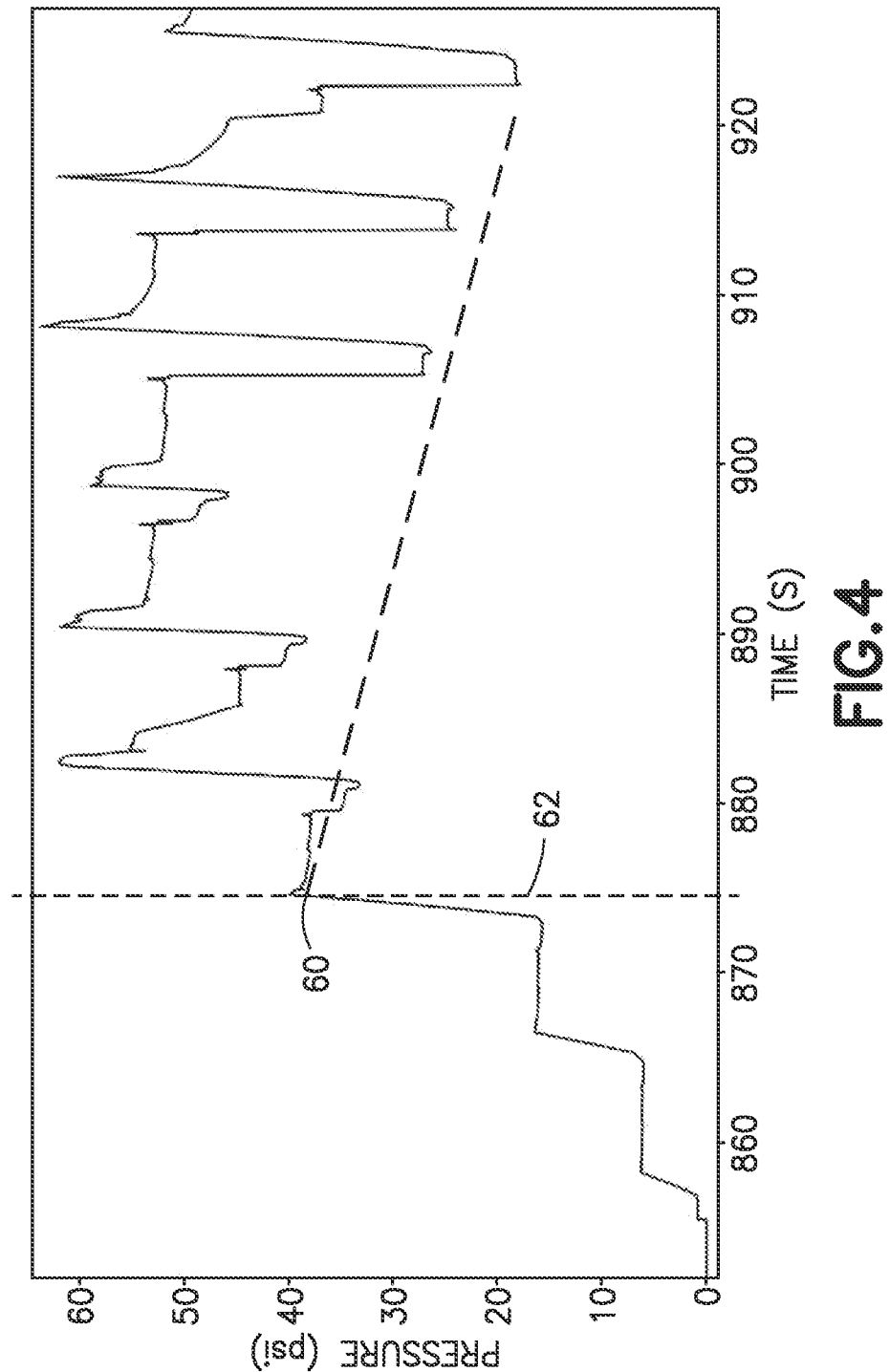
FIG. 4 is a graph of pressure versus time for the drug delivery device of FIG. 1, showing a method of pressure management according to one aspect or embodiment of the present application.
Figure 6:
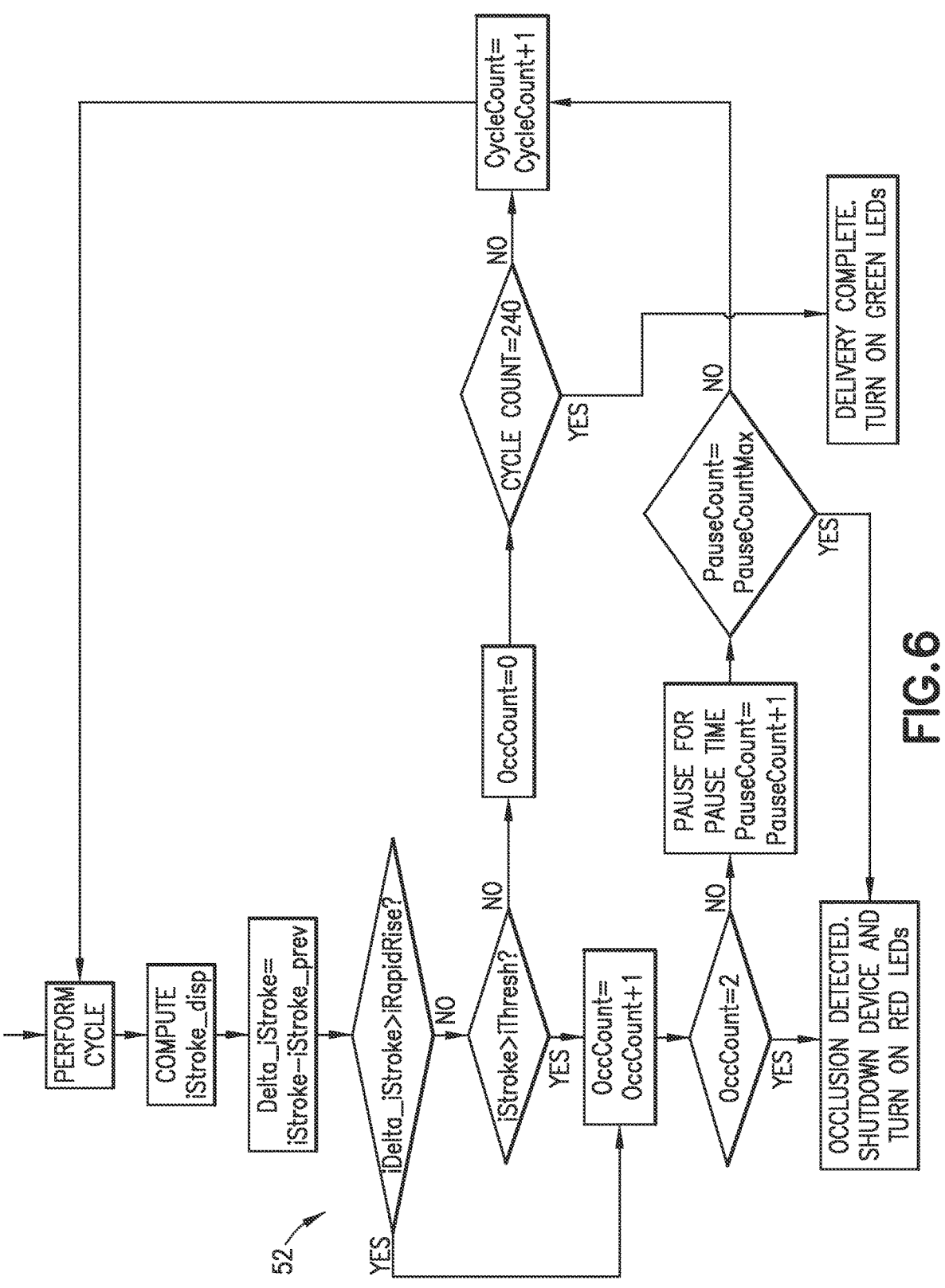
FIG. 6 is a further schematic view of the method of FIG. 5.

Referring to FIGS. 4-6, in one aspect or embodiment, a method 52 of pressure management for the drug delivery device 10 includes: delivering fluid through the fluid line 50 via the pump and valve mechanism 42; determining a pressure within the fluid line 50; determining whether the pressure within the fluid line 50 exceeds a pressure threshold level; pausing the delivery of fluid through the fluid line 50 until a predetermined condition is satisfied; and resuming the delivery of the fluid through the fluid line 50 after the predetermined condition is satisfied. The predetermined condition may be a predetermined period of time, although the predetermined condition may also be a predetermined pressure level within the fluid line 50, or the predetermined condition may be an input from a sensor in the device or an input from a user. The pressure level within the fluid line 50 may be continuously monitored utilizing a sensor or other arrangement, although the pressure may also be determined based on the current utilized during actuation of the device 10, as discussed in additional detail below. As shown in FIG. 4, when the pressure within the fluid line 50 reaches the pressure threshold level 60, a pause 62 of the delivery of the fluid is initiated to let the pressure naturally decay, when possible, to a level at which the delivery of fluid can be resumed. The algorithm logic of the method 52 is shown in FIGS. 5 and 6. The method 52 may include one or more iterative processes from the beginning of the delivery of the fluid to the completion of the delivery of the full dose of fluid. The method 52 may be executed by the microcontroller 24 or other processor of the drug delivery device 10.

In one aspect or embodiment, the method 52 includes terminating the delivery of fluid through the fluid line 50 when the delivery of fluid has been paused for a maximum delay period. For example, if the delivery of the fluid is paused until the pressure within the fluid line 50 falls below the predetermined pressure level and the pressure within the fluid line 50 does not fall below the predetermined pressure level after the maximum delay period, the delivery process is terminated and an error or occlusion indication may be provided by the drug delivery device 10. In one aspect or embodiment, the maximum delay period is at least 30 seconds. In another aspect or embodiment, the maximum delay period is at least 4 minutes. In one aspect or embodiment, the delivery of the fluid is provided via a plurality of smaller deliveries and the maximum delay period includes the total amount of time or total number of delay periods between these discrete deliveries. For example, if the delivery of fluid is paused for the predetermined amount of time due to the pressure within the fluid line 50 exceeding the pressure threshold level 60, a subsequent bolus may be delivered and, if the pressure continues to exceed the pressure threshold level 60, the delivery may be terminated. The delivery may be terminated after one or more subsequent bolus deliveries when the delivery has been paused and fails to fall below the pressure threshold level 60.

Figure 7:
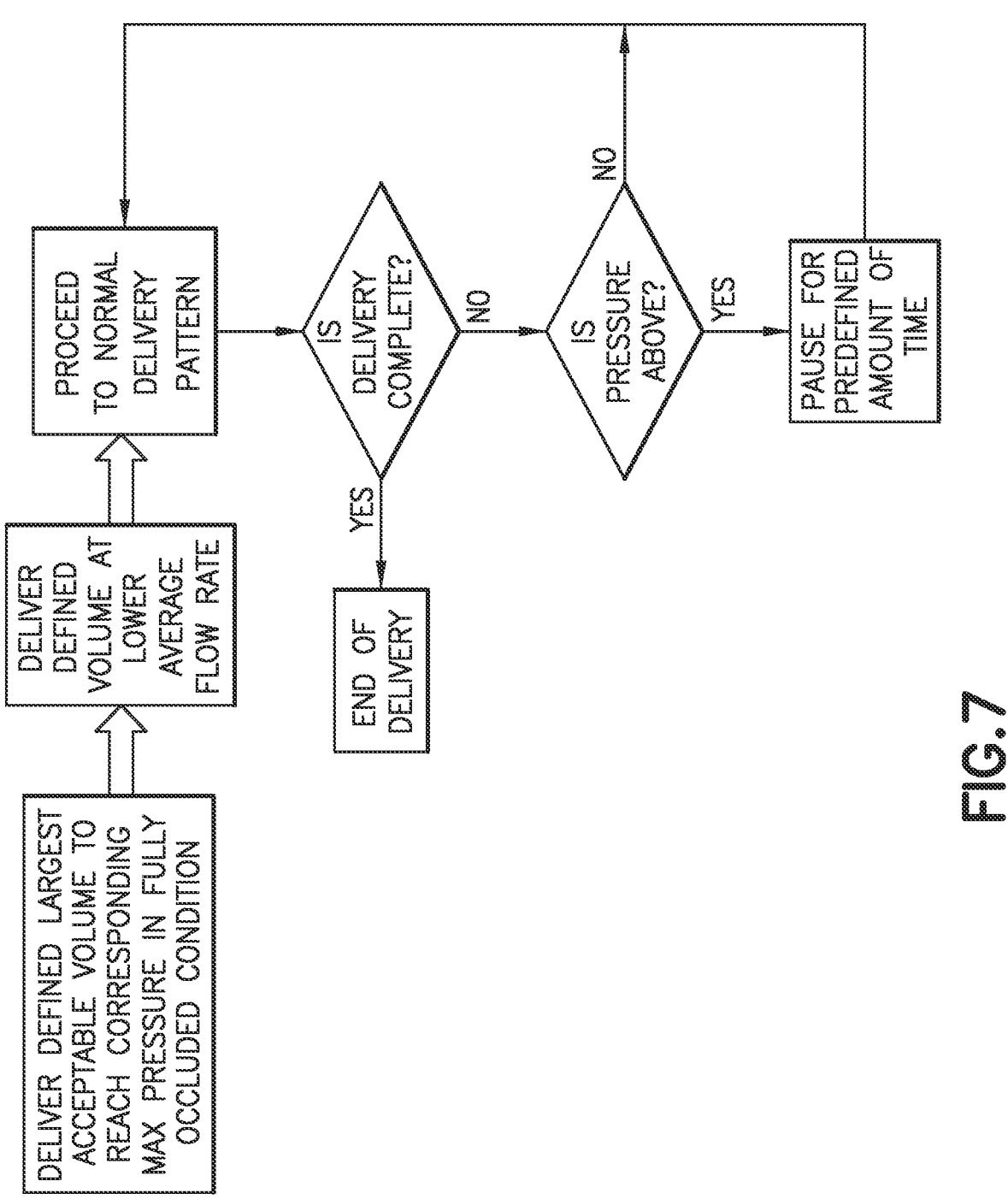
FIG. 7 is a schematic view of a method of pressure management according to a second aspect or embodiment of the present application.

Referring to FIG. 7, in one aspect or embodiment, the method 52 may further include initially delivering fluid through the fluid line 50 via the pump and valve mechanism 42 at a first flow rate, and subsequently delivering fluid through the fluid line 50 via the pump and valve mechanism 42 at a second flow rate, where the first flow rate is lower than the second flow rate. After delivering the fluid at the second flow rate, the method 52 discussed above in FIGS. 4-6 may continue until delivery is complete or until an occluded condition is determined. When biological tissue is infiltrated with fluid, its mechanical and absorption properties are modified by the fluid. The infiltrated tissue typically displays lower resistance to further infiltration of fluid. Accordingly, peak infusion pressures typically occur at the beginning of the delivery and prior to any fluid entering the target tissue. Accordingly, by providing the first flow rate at the beginning of the delivery, the pressure within the fluid line 50 can be preemptively managed. In one aspect or embodiment, the initial delivery of fluid through the fluid line 50 at the first flow rate is configured to deliver 15-50 μL of fluid. In one aspect or embodiment, the initial delivery of fluid through the fluid line 50 at the first flow rate includes pausing 62 the delivery of fluid for a predetermined delay period between delivery boluses.

In one aspect or embodiment, the first flow rate corresponds to a maximum acceptable flow rate assuming a fully occluded condition. After delivery of a known volume, such as 20 μL of fluid, the delivery is paused 62 for a period of time, such as 1 minute, before resuming delivery at the second flow rate. The delivery of 20 μL of fluid may correspond to four actuation cycles of the pump and valve mechanism 42.

Figure 8A:
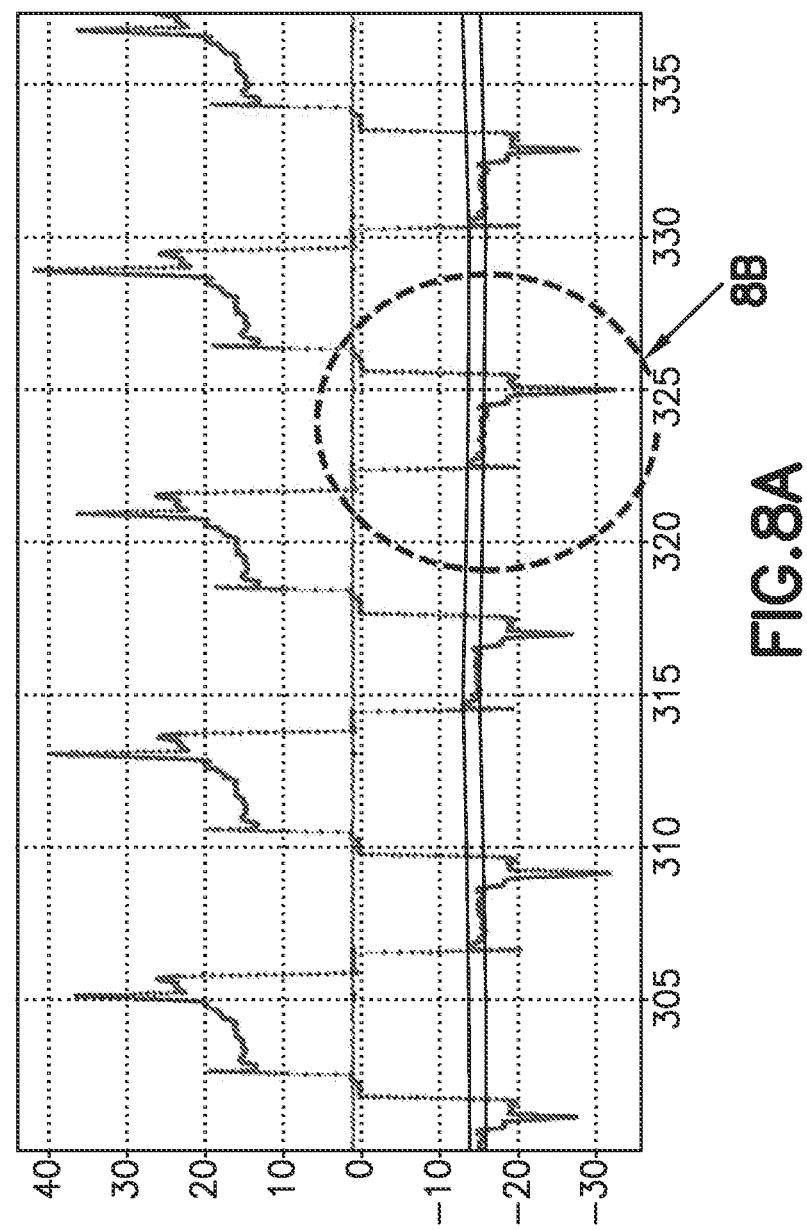
FIG. 8A is a graph of current versus time for the drug delivery device of FIG. 1, showing a method of determining fluid path pressure according to one aspect or embodiment of the present application.
Figure 8B:
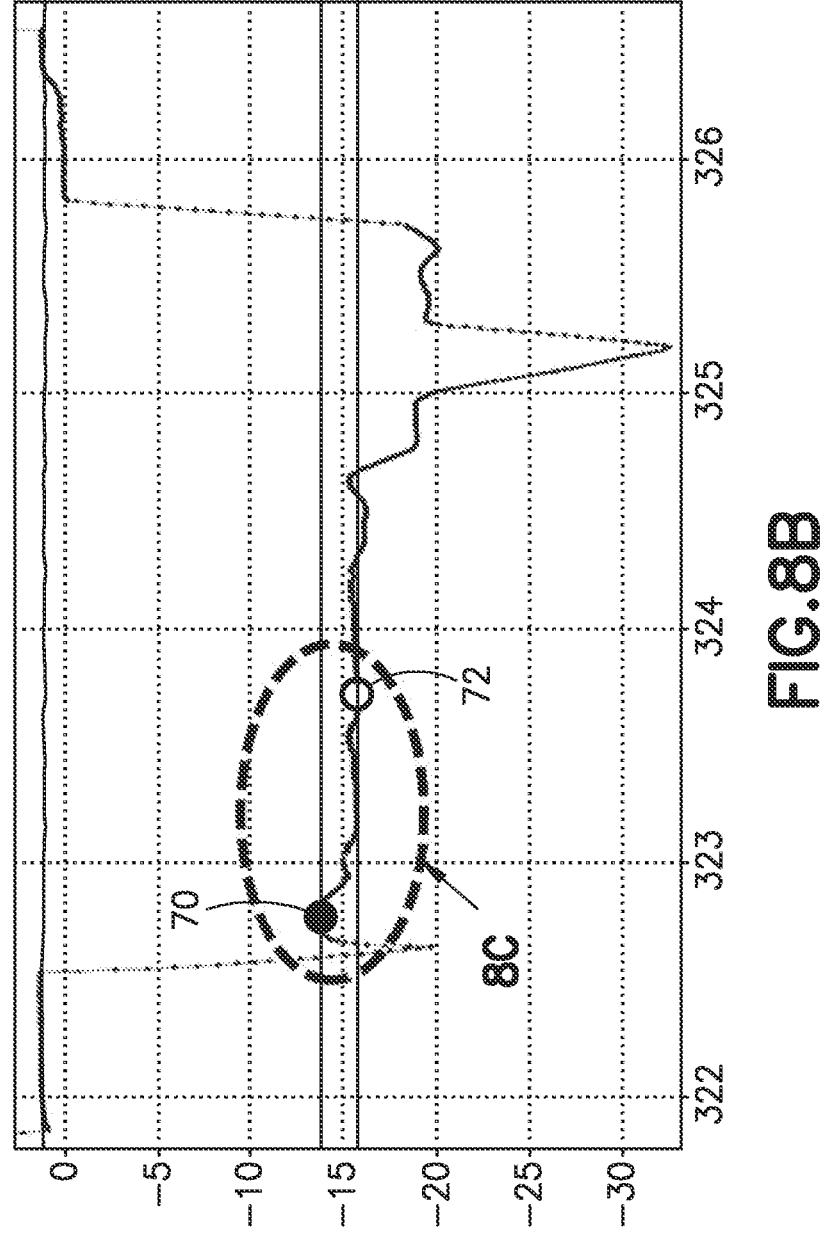
FIG. 8B is an enlarged graph of area 8B shown in FIG. 8A.
Figure 8C:
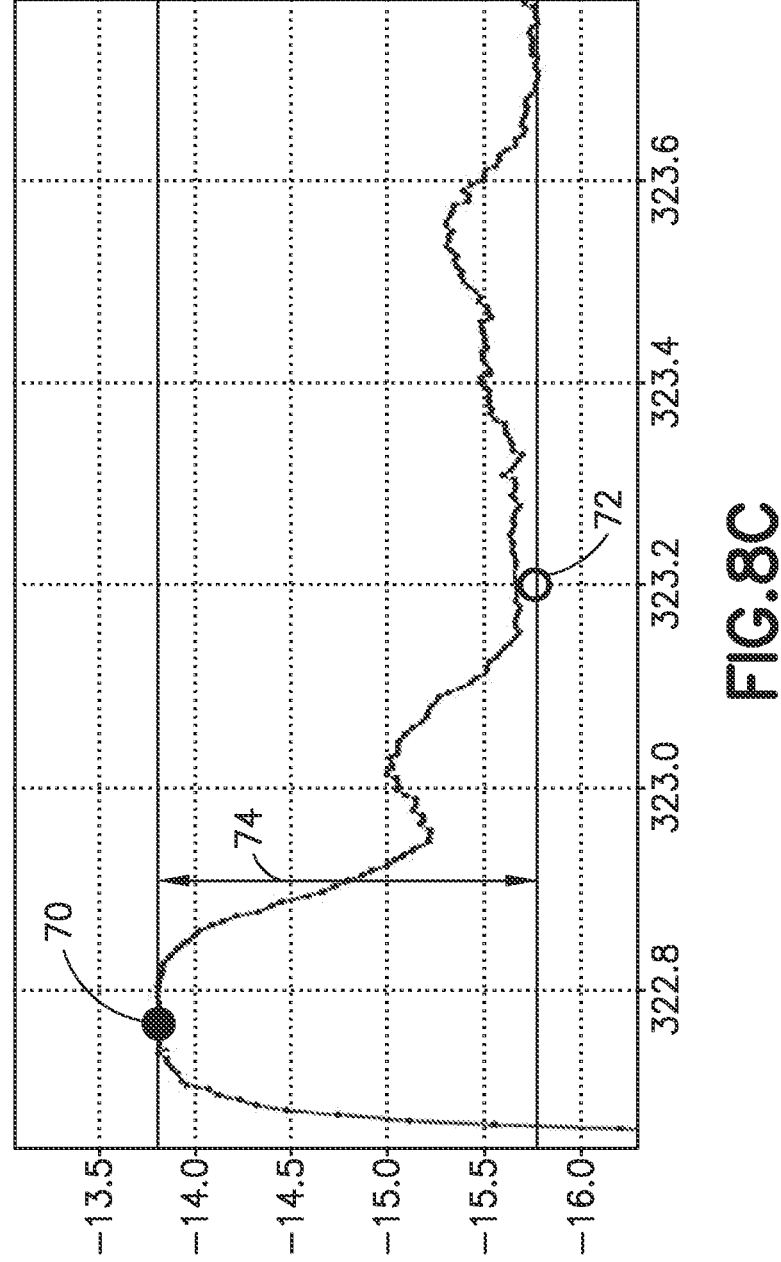
FIG. 8C is an enlarged graph of area 8C shown in FIG. 8B.

Referring to FIGS. 8A-8C, in one aspect or embodiment, the pressure within the fluid line 50 is determined by measuring a parameter indicative of pressure, such as directly measuring the pressure or measuring a current of the drug delivery device 10 during actuation of the pump and valve mechanism 42. The measuring of the current of the drug delivery device 10 includes subtracting a reference or baseline current value 70 from a peak current value 72 during an actuation cycle of the pump and valve mechanism 42 to determine a stroke current value 74, although other suitable current detection arrangements may be utilized. The stroke current value 74 is utilized to estimate the downstream pressure of the fluid line 50 for the particular actuation cycle of the pump and valve mechanism 42. For example, the stroke current value 74 can be corresponded to various downstream pressure levels through testing or benchmarking such that the stroke current value 74 can be used to accurately estimate the pressure level of the fluid line 50.

The device 10 and method 52 provides for the management of the maximum pressure and overall pressure profile during the delivery process with a low cost of manufacture, a low occurrence of false occlusion alarms, broadens the effective operation range of the drug delivery device 10, and allows for optimal delivery time without causing leaks within the device 10.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method of pressure management for a drug delivery device comprising a pump, a fluid line, and a power source, the method comprising:
   a) delivering fluid through the fluid line via the pump;
   b) determining a parameter indicative of pressure within the fluid line;
   c) determining whether the parameter is indicative of pressure within the fluid line exceeds a pressure threshold level;
   d) pausing the delivery of fluid through the fluid line until a predetermined condition is satisfied; and
   e) resuming the delivery of the fluid through the fluid line after the predetermined condition is satisfied,
   wherein the parameter indicative of pressure within the fluid line is determined by measuring a current of the drug delivery device during actuation of the pump, and wherein the measuring of the current of the drug delivery device comprises subtracting a reference current value from a peak current value during an actuation cycle of the pump to determine a stroke current value.

2. The method of claim 1, further comprising terminating the delivery of fluid through the fluid line when the delivery of fluid has been paused for a maximum delay period.

3. The method of claim 2, wherein the maximum delay period is at least 30 seconds.

4. The method of claim 1, wherein the predetermined condition comprises a predetermined pressure level within the fluid line.

5. The method of claim 1, wherein the predetermined condition comprises a predetermined period of time.

6. The method of claim 1, further comprising:
   initially delivering fluid through the fluid line via the pump at a first flow rate; and
   subsequently delivering fluid through the fluid line via the pump at a second flow rate, wherein the first flow rate is lower than the second flow rate.

7. The method of claim 6, wherein the initial delivery of fluid through the fluid line via the pump at the first flow rate is configured to deliver 15-50 μL of fluid.

8. The method of claim 6, wherein the initial delivery of fluid through the fluid line via the pump at the first flow rate comprises pausing the delivery of fluid for a predetermined delay period between delivery boluses.

9. The method of claim 6, wherein the first flow rate corresponds to a maximum acceptable flow rate assuming a fully occluded condition.

10. The method of claim 9, wherein the initial delivery of fluid through the fluid line via the pump at the first flow rate is configured to deliver a maximum of 20 μL of fluid.

11. The method of claim 1, wherein at least one of b) through e) are performed using a microcontroller comprising at least one processor.

12. A drug delivery device comprising:

a power source;

a reservoir configured to receive a fluid;

a fluid line in fluid communication with the reservoir;

a pump configured to deliver the fluid from the reservoir to the fluid line; and a microcontroller comprising at least one processor programmed or configured to cause the device to:

deliver fluid through the fluid line via the pump;

determine a parameter indicative of pressure within the fluid line;

determine whether the parameter indicative of pressure within the fluid line exceeds a pressure threshold level;

pause the delivery of fluid through the fluid line until a predetermined condition is satisfied; and resume the delivery of the fluid through the fluid line after the predetermined condition is satisfied, wherein the parameter indicative of pressure within the fluid line is determined by measuring a current of the drug delivery device during actuation of the pump, and wherein the measuring of the current of the drug delivery device comprises subtracting a reference current value from a peak current value during an actuation cycle of the pump to determine a stroke current value.

13. The device of claim 12, wherein the at least one processor is further programmed or configured to:

initially deliver fluid through the fluid line via the pump at a first flow rate; and subsequently delivery fluid through the fluid line via the pump at a second flow rate, wherein the first flow rate is lower than the second flow rate.

14. The device of claim 13, wherein the at least one processor is further programmed or configured to pause the delivery of fluid for a predetermined delay period between delivery boluses.

15. The device of claim 13, wherein the first flow rate corresponds to a maximum acceptable flow rate assuming a fully occluded condition.

16. A computer program product for a method of pressure management for a drug delivery device comprising a microcontroller, a reservoir, a pump, a fluid line, and a power source, the computer program product comprising at least one non-transitory computer-readable medium including program instructions that, when executed by the microcontroller, cause the drug delivery device to:

deliver fluid through the fluid line via the pump;

determine a parameter indicative of pressure within the fluid line;

determine whether the pressure within the fluid line exceeds a pressure threshold level;

pause the delivery of fluid through the fluid line until a predetermined condition is satisfied; and resume the delivery of the fluid through the fluid line after the predetermined condition is satisfied, wherein the parameter indicative of pressure within the fluid line is determined by measuring a current of the drug delivery device during actuation of the pump, and wherein the measuring of the current of the drug delivery device comprises subtracting a reference current value from a peak current value during an actuation cycle of the pump to determine a stroke current value.

17. The computer program product of claim 16, wherein the at least one non-transitory computer-readable medium further includes program instructions that, when executed by the microcontroller, cause the microcontroller to:

initially deliver fluid through the fluid line via the pump at a first flow rate; and subsequently delivery fluid through the fluid line via the pump at a second flow rate, wherein the first flow rate is lower than the second flow rate.

18. The computer program product of claim 17, wherein the at least one non-transitory computer-readable medium further includes program instructions that, when executed by the microcontroller, cause the microcontroller to pause the delivery of fluid for a predetermined delay period between delivery boluses.

19. The computer program product of claim 17, wherein the first flow rate corresponds to a maximum acceptable flow rate assuming a fully occluded condition.

20. The computer program product of claim 16, wherein the parameter indicative of pressure threshold level comprises a threshold, range, and/or rate of pressure increase.

* * * * *